United States Patent [19]

Sheth et al.

[11] Patent Number: 4,867,979
[45] Date of Patent: Sep. 19, 1989

[54] ANTIDIARRHEAL COMPOSITIONS AND USE THEREOF

[75] Inventors: Bhogilal B. Sheth, Norwalk; Sheri A. Gilbert, Stratford; Jane F. Kinsel, Derby, all of Conn.

[73] Assignee: Richardson-Vicks Inc., Wilton, Conn.

[21] Appl. No.: 913,755

[22] Filed: Sep. 30, 1986

Related U.S. Application Data

[62] Division of Ser. No. 646,832, Sep. 4, 1984, Pat. No. 4,666,716.

[51] Int. Cl.$^4$ .................. A61K 35/78; A61K 31/715; A61K 31/60; A61K 31/54

[52] U.S. Cl. .............................. 424/195.1; 514/57; 514/159; 514/165; 514/403; 514/466; 514/415; 514/429; 514/532; 514/553; 514/567; 514/568; 514/579; 514/867; 514/226.5

[58] Field of Search ............... 424/195.1; 514/57, 867, 514/165, 159, 222, 396, 466, 403, 420, 532, 429, 567, 568, 579, 553, 415

[56] References Cited

U.S. PATENT DOCUMENTS 4,588,589 5/1986 Sheth ............................... 424/195.1

Primary Examiner—John Rollins
Attorney, Agent, or Firm—George W. Rauchfuss, Jr.

[57] ABSTRACT

Antidiarrheal compositions showing enhanced antidiarrheal activity comprise a non-steroidal anti-inflammatory drug compound and a polymeric hydroabsorptive agent. A patient in need of remedial or preventive treatment of diarrhea symptoms is administered an antidiarrheally effective amount of said antidiarrheal compositions.

22 Claims, 1 Drawing Sheet

ISOBOLOGRAM FOR THE COMBINATION OF IBUPROFEN (IBF) AND PSYLLIUM (PS) (1 HOUR POST-CHALLENGE)

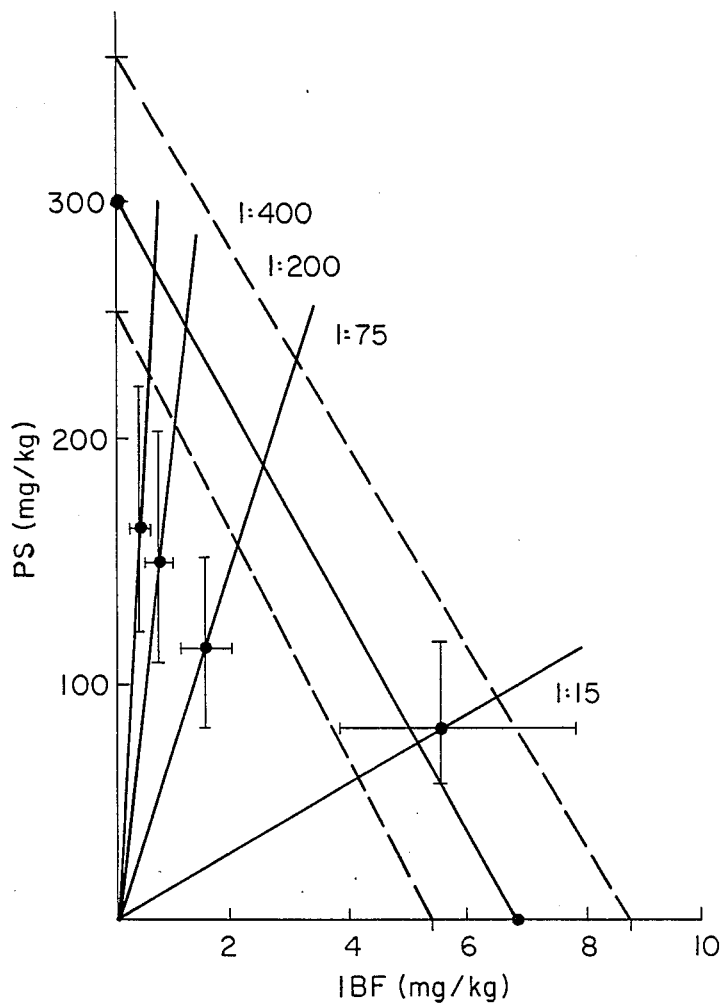

ANTIDIARRHEAL COMPOSITIONS AND USE THEREOF

This is a division of application Ser. No. 646,832, filed Sept. 4, 1984, now U.S. Pat. No. 4,666,716.

FIELD OF THE INVENTION

This invention relates to antidiarrheal compositions of enhanced antidiarrheal activity and to the use thereof to treat a patient in need of preventative or remedial treatment of diarrhea symptoms.

BACKGROUND OF THE INVENTION

Diarrhea can result from a variety of pathophysiological disorders including bacterial and parasitic infections, disease or debilitation of organs such as liver, adrenal and others. It can also occur as a result of other therapy or diet. In all cases, diarrhea is generally a symptom of organic gastrointestinal disorders and not itself a disorder. Chronic diarrhea is generally due to intestinal hypermotility and rapid transport. It may also be due to, or accompanied by hypersecretion of acid gastric juices or decreased reabsorption and may, in some instances, particularly those accompanied by hypersecretion, be associated with emotional tension and psychological conflicts.

Antidiarrheal compounds are, of course, wellknown in the medicinal arts and take various forms. In particular there are a variety of products known which act systemically to provide antidiarrheal effects when administered in a manner which will enable the drug to be taken into the system at effective therapeutic levels.

It is becoming increasingly evident from the literature that non-steroidal anti-inflammatory drugs (NSAID) are effective antidiarrheal agents, but generally, only at high doses. It would be highly desirable, however, if the antidiarrheal doses of the NSAID were much lower than those typically reported for their anti-inflammatory or analgesic activity and the antidiarrheal activity of these NSAID could be potentiated so as to provide more effective antidiarrheal activity.

SUMMARY OF THE INVENTION

Antidiarrheal compositions of enhanced antidiarrheal activity are provided by compositions of a NSAID and a polymeric hydroabsorptive agent. Administration of an antidiarrheally effective amount of said compositions to patients would provide remedial or preventive treatment of diarrhea symptoms.

DETAILS OF THE INVENTION

The antidiarrheal activity of NSAID compounds has been found to be unexpectedly potentiated when administered concurrently with a polymeric hydroabsorptive agent. Preferred hydroabsorptive agents are nonionic polymeric hydroabsorptive agents and still more preferred hydroabsorptive agents are psyllium and glucomannan. Especially preferred in psyllium.

Psyllium (plantagoe seed) useful in the compositions of this invention is described in Pharmacopeia XX, page 634, U.S. Pharmacopeial Convention, Inc., 1980. Glucomannan useful in the compositions of this invention is described in the article titled "Japanese Diet Food" on page 22 of the September 1980 issue of Food Engineering. Glucomannan is a hydrophilic hemicellulose extract from the knojac root and is sold as an appetite curb under the trademark Regal Mannan by Regal Vitamin Co., Costa Mesa, Calif.

The NSAID compounds whose antidiarrheal activity is potentiated by a polymeric hydroabsorptive agent of this invention vary widely in their chemical structure and in their biological profiles as analgesics, anti-inflammatory agents and antipyretic agents. Among the classes of NSAID compounds found useful in the compositions of this invention there may be mentioned for example, salicylic acid derivatives, propionic acid derivatives, indole and pyrole acetic acid derivatives, pyrazole derivatives, fenamate derivatives, oxicam derivatives, phenylacetamide derivatives and the like. Among the members of this group of NSAID compounds there may be mentioned for example, aspirin, salsalate, sodium salicylate, magnesium salicylate, acetaminophen, phenacetin, diflunisal, zomepirac sodium, ibuprofen, naproxen, fenoprofen calcium, piroxicam, flurbiprofen, mefenamic acid, sulindac, fenbufen, ketoprofen, tolmetin sodium, indomethacin, meclofenamate sodium, phenylbutazone, and the like.

Especially preferred NSAID compounds in the antidiarrheal compositions of this invention are aspirin, indomethacin and ibuprofen.

While this invention envisions any antidiarrheally effective potentiating combination combination of NSAID compound and polymeric hydroabsorptive agents, the relative amounts of NSAID compound to polymeric hydroabsorptive agent in the compositions of this invention that provide the enhanced antidiarrheal activity is in the range of ratio of NSAID compound to polymeric hydroabsorptive agent of from about 1:30 to about 1:600, more preferably from about 1:75 to about 1:400 and most preferably from about 1:100 to about 1:200.

The compositions of the present invention can be prepared in forms suitable for administration to humans and animals by compounding an effective single dose amount of the composition of the active ingredients of this invention with known ingredients generally employed in the preparation of therapeutic compositions provided as tablets, capsules, lozenges, chewable lozenges, pills, powder, granules, suspensions, or other similar forms which can be taken orally. In general the composition of the active ingredients of this invention above are indicated for use as pharmacotherapeutic agents in a wide variety of mammalian conditions which require relief of diarrhea symptoms accompanying abnormal action of the gastrointestinal system.

The dosage regimens in carrying out the pharmcotherapeutic methods utilizing the compositions of this invention are those which insure maximum therapeutic response until improvement is obtained and thereafter the minimum effective level which gives relief. Thus, in general, the dosages are those that are therapeutically effective in the treatment of diarrhea. In general, the single oral dose may contain up to the usual therapeutic limit of the individual NSAID in combination with the appropriate amount of polymeric hydroabsorptive agent to achieve the appropriate ratios. For example, at the 1:30 ratio, 400 mg ibuprofen might be combined with 12 g polymer whereas 50 mg indomethacin might be combined with 1.5 g polymer. At the other extreme, at an NSAID/polymer ratio of about 1:600, as little as 1 mg ibuprofen plug 600 mg polymer might be an effective dose. The preferred dose levels would be those that achieve optimal clinical antidiarrheal effectiveness at the lowest NSAID dose. The NSAID compound and the polymeric hydroabsorptive agent may be administered concurrently or together as a single formulation. Fractional or multiple doses can of course be given bearing in mind that in selecting the appropriate dosage in any specific case, consideration must be given to the patient's weight, general health, age, and other factors which may influence response to the drug. The drug response on oral administration usually follows within the first hour after administration and may be maintained for up to about 4 hours. The drug is generally given in single doses up to 8 times daily or as required to maintain effective continuous relief of diarrhea symptoms.

Compositions intended for oral use may be prepared according to methods known generally in the art. Such compositions may contain one or more agents selected from the group consisting of sweetening agents, flavoring agents, coloring agents and preserving agents, in order to provide a pharmaceutically elegant and palatable preparation. Orally, they may be administered in tablets, lozenges, oily suspensions, dispersible powders or granules, or hard or soft capsules which contain the active ingredients in admixture with non-toxic pharmaceutically acceptable excipients. Excipients which may be, for example, inert diluents, such as calcium carbonate, magnesium carbonate, calcium phosphate, calcium sulphate, lactose, cellulose, microcrystalline cellulose, starch, modified starch dextrose, sucrose, mannitol, sorbitol; binding agents, for example, polyvinyl pyrrolidone, cellulose ethers such as sodium carboxymethyl-cellulose, methyl cellulose, hydroxypropyl cellulose, hydroxypropylmethyl cellulose, hydroxy ethyl cellulose and ethyl cellulose, natural gums such as acacia, tragacanth, pectin, guar and karaya, gelatin, alginates, starch, modified starch, polyethylene glycol, microcrystalline cellulose, sugars such as sucrose, sorbitol and glucose, corn syrups, polyvinyl alcohols, polyacrylamides, or polyvinyloxoazolidone; disintegrants, such as, cross linked polyvinyl pyrrolidone, sodium starch glycollate, cross-linked carboxymethyl cellulose, ion exchange resins, starch, modified starches, microcrystalline cellulose, cellulose, cellulose derivatives, alginates, alginic acid or clays; lubricants, glidants and antiadherants, such as for example, silicone fluids, hydrogenated vegetable oils, light mineral oil, microfine silicas, metallic stearates, stearic acid, polyethylene glycol, talc, corn starch, sodium benzoate, sodium acetate, polyoxyethylene monostearate, magnesium carbonate or magnesium oxide. The tablets may be uncoated or they may be coated by known techniques to make them more effective, to delay disintegration or absorptionor to make them more palatable or for other reasons for which orally administered drugs have been previously provided in coated form.

Formulations for oral use may also be presented as hard gelatin capsules wherein the active ingredient is mixed with an inert solid diluent, binding agent, disintegrant, lubricant, glidant or anti-adherent as described hereinbefore for tablets, or as soft gelatin capsules wherein the active ingredient is mixed with an oil medium, for example, arachis oil, liquid paraffin or olive oil.

Oily suspensions may be formulated by suspending the composition of the active ingredients in a vegetable oil, for example, arachis oil, olive oil, sesame oil or coconut oil, or in a mineral oil, such as liquid paraffin. The oil suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredients in admixture with dispersing, wetting agent or suspending agents. These excipients are suspending agents, for example, sodium carboxymethyl cellulose, hydroxypropyl methylcellulose, sodium alginate, polyvinylpyrrolidine, gum tragacanth and gum acacia; dispersing or wetting agents may be a naturally occurring phosphatide, for example, lecithin; or condensation products or an alkylene oxide with fatty acids, for example, polyoxyethylene stearate; or condensation products of ethylene oxide with long-chain aliphatic alcohols, for example, heptadecaethyleneoxy-cetanol; or condensation products of ethylene oxide with partial esters derived from fatty acids and a hexitol, for example, polyoxyethylene sorbitol monooleate; or condensation products of ethylene oxide with partial esters derived from fatty acids and hexitol anhydrides, for example, polyoxyethylene sorbitan monooleate. They may also include one or more preservatives, for example, ethyl, or n-propyl, p-hydroxy benzoate, one or more coloring agents, one or more flavoring agents, and one or more sweetening agents, such as sucrose.

Generally, these compositions may be tableted or otherwise formulated for oral use so that for every 100 parts by weight of the composition, there are present between 5 and 95 parts by weight of the active ingredients.

The enhanced antidiarrheal activity for the compositions of this invention was shown by a castor oil-induced diarrheal test in rats which is a modified test described by Niemegeers et al., ArzneimForsch 22, 516-518 (1972). The modified test was as follows. An NSAID compound, such as aspirin (ASA), indomethacin (I) or Ibuprofen (IBF) and a polymeric hydroabsorptive agent, such as psyllium (PS) or glucomannan (GM) were evaluated alone and in NSAID/polymeric agent ratios of 1:75, 1:200, 1:400 and 1:600. The test materials were suspended in 0.25% methocellulose and administered to groups of 10 to 45 fasted rats via oral intubation. One hour following treatment, each rat was given 1.0 ml of castor oil via intubation and placed into an individual cage lined with absorbent paper. The papers were examined and replaced hourly up to 6 hours following the castor oil challenge. Antidiarrheal activity was expressed quantally as an "all-or-none response"; once an animal demonstrated evidence of diarrhea, that animal was considered to be unprotected at all subsequent time points.

Median effective antidiarrheal doses ($ED_{50}$'s) were determined hourly for up to six hours posttreatment for the individual ingredients and for the combinations on the basis of the dose response data generated in the aforementioned test regimen. Drug interactions were evaluated according to the model proposed by Finneyl, Probit Analysis, Cambridge Univ. Press, 3rd Edition (1971) and Bliss, Ann. Appl. Biol., 26, pp 585–615 (1939). When the slopes of the dose-response data for the individual drugs and their combination were parallel, the data were analyzed according to the model of simple similar action. In those cases where significant non-parallelism occurred, the data were analyzed according to the model of independent joint action.

RESULTS

The $ED_{50}$'s of the individual drugs and the actual and predicted $ED_{50}$'s of the combinations are tabulated below; except where indicated, the data were analyzed according to the model of simple similar action:

| Combination | Ratio | $ED_{50}$ Values (mg/kg) Actual (NSAID + Polymer) | Predicted NSAID + Polymer | Relative Potency |
|---|---|---|---|---|
| IBF/PS (1 hour) | Individual Drugs | IBF PS 6.9 293 | — | — |
| | 1:75 | 113(1.5 + 112) | 191(2.5 + 188) | 1.69 |
| | 1:200 | 147(0.7 + 146) | 243(1.2 + 241) | 1.65 |
| | 1:400 | 162(0.4 + 162) | 266(0.7 + 265) | 1.64 |
| IBF/PS (2 hour) | Individual Drugs | IBF PS 51 1055 | — | — |
| | 1:400 | 539(1.3 + 538) | 1003(2.5 + 1000) | 1.86 |
| IBF/GM[1] (1 hour) | Individual Drugs | IBS GM 6.9 225 | — | — |
| | 1:600 | 162(0.3 + 162) | 225(0.4 + 224) | 1.39 |
| ASA/PS (1 hour) | Individual Drugs | ASA PS 3.0 298 | — | — |
| | 1:75 | 102(1.3 + 101) | 131(1.7 + 129) | 1.28 |
| | 1:200 | 129(0.6 + 128) | 201(1.0 + 200) | 1.56 |
| I/PS (1 hour) | Individual Drugs | I PS 0.44 447 | — | — |
| | 1:400 | 30(0.07 + 29.93) | 125(0.31 + 124.7) | 4.22 |
| I/PS (2 hour) | Individual Drugs | I PS 6.29 1076 | — | — |
| | 1:400 | 353(0.88 + 352.1) | 741(1.85 + 739.2) | 2.14 |
| I/PS (4 hour) | Individual Drugs | I PS 24.67 10413 | — | — |
| | 1:400 | 1184(2.95 + 1181) | 5091(12.7 + 5078) | 4.29 |

[1] Because of significant non-parallelism, the data did not fit the model of simple similar action and were analyzed for independent joint action.

Based on the relative potency of the actual value to the predicted values, significant enhancement of activity was found with ibuprofen/psyllium ratios of 1:75, 1:200 and 1:400. The activity of the combinations at 1 hour was 64–69% greater than expected on the basis of the individual components. At 2 hours, the activity of the 1:400 ratio was 86% greater than expected. The interaction for ibuprofen and psyllium at 1 hour post challenge is demonstrated by data in Loewe isobolograms (S. Loewe: Pharm. Rev. 9:237–242, 1957) in the drawing. In the drawing, the diagonal line joining the $ED_{50}$ values of the two drugs given separately represents simple additivity of drug effects. The dashed lines on each side of the diagonal line give the 95% confidence limits for this line of additivity. $ED_{50}$'s of combinations falling under the curve (between the lower dashed line and the origin) indicate potentiation (unexpected enhancement) of effects while those above the upper dashed line would suggest antagonism between the two drugs. The four diagonal lines radiating from the origin represent the dose ratios of ibuprofen to psyllium used in rats receiving the combined drug dosages. The horizontal and vertical bars through each $ED_{50}$ point are the 95% confidence limits. The visual estimates from the isobologram of the drawing indicate that in the method of the invention compositions having a ratio of a NSAID compound, such as ibuprofen to a polymeric hydroabsorptive agent, such as psyllium, of from about 1:30 to greater than 1;400 give unexpectedly enhanced activity.

The relative potency data in the hereinbefore set forth table shows that the combination of indomethacin with hydroabsorptive polymer psyllium was up to four times more active than predicted based on addition of the activities of indomethacin and psyllium at 1, 2 and 4 hours. Also the activity of the combination of ibuprofen and glucomannan was 37% greater than expected based on the activities of the individual components and the activity of the combination of aspirin and psyllium was from 28 to 56% greater than expected based on the activities of the individual components.

We claim:

1. An antidiarrheal composition comprising an antidiarrheal effective amount of a non-steroidal antiinflammatory drug (NSAID) selected from the group consisting of derivatives of salicylic acid, imidole and pyrrole acetic acids, pyrazole, oxicam and phenylacetamide derivatives and a nonionic polymeric hydroabsorptive agent selected from the group consisting of psyllium and glucomannan, wherein the weight ratio of said NSAID to said hydroabsorptive agent is in the range of from about 1:30 to about 1:600.

2. A composition of claim 1 wherein the hydroabsorptive agent is psyllium.

3. A composition of claim 2 wherein the weight ratio of NSAID to psyllium is about 1:75 to about 1:400.

4. A composition of claim 3 wherein the NSAID is selected from the group consisting of indomethacin, and aspirin.

5. A composition of claim 4 wherein the NSAID is indomethacin.

6. A composition of claim 1 wherein the hydroabsorptive agent in glucomannan.

7. A composition of claim 6 wherein the weight ratio of NSAID to glucomannan is about 1:75 to about 1:400.

8. A composition of claim 7 wherein the NSAID is selected from the group consisting of indomethacin, and aspirin.

9. A composition of claim 8 wherein the NSAID is indomethacin.

10. A composition of claim 1 wherein the weight ratio of NSAID by hydroabsorptive agent is about 1:75 to about 1:400.

11. A composition of claim 1 wherein the NSAID is selected from the group consisting of aspirin, salsalate, sodium salicylate, magnesium salicylate, acetaminophen, phenacetin, diflunisal, zomepirac sodium, piroxicam, mefenamic acid, sulindac, tolmetin sodium, indomethacin, meclofenamate sodium and phenylbutazone.

12. A method for the remedial or preventive treatment of diarrheal symptoms comprising concurrently administering to a host in need thereof an antidiarrheal effective amount of a non-steroidal antiinflammatory drug (NSAID) selected from the group consisting of derivatives of salicylic acid, imidole and pyrrole acetic acids, pyrazole, oxicam and phenylacetamide derivatives and a nonionic polymeric hydroabsorptive agent selected from the group consisting of psyllium and glucomannan, wherein the weight ratio of said NSAID to said hydroabsorptive agent is in the range of from about 1:30 to about 1:600.

13. A method of claim 12 wherein the hydroabsorptive agent is psyllium.

14. A method of claim 13 wherein the weight ratio of NSAID to psyllium is about 1.75 to about 1:400.

15. A method of claim 14 wherein the NSAID is selected from the group consisting of indomethacin, and aspirin.

16. A method of claim 15 wherein the NSAID is indomethacin.

17. A method of claim 12 wherein the hydroabsorptive agent is glucomannan.

18. A method of claim 17 wherein the weight ratio of NSAID to glucomannan is about 1.75 to about 1:400.

19. A method of claim 12 wherein the weight ratio of NSAID to hydroabsorptive agent is about 1:75 to about 1:400.

20. A method of claim 19 wherein the NSAID is selected to the group consisting of indomethacin, and aspirin.

21. A method of claim 20 wherein the NSAID is indomethacin.

22. A method of claim 12 wherein the NSAID is selected from the group consisting of aspirin, salsalate, sodium salicylate, magnesium salicylate, acetaminophen, phenacetin, diflunisal, zomepirac sodium, piroxicam, mefenamic acid, sulindac, tolmetin sodium, indomethacin, meclofenamate sodium and phenylbutazone.

* * * * *